(12) United States Patent
Samaroo

(10) Patent No.: US 6,305,216 B1
(45) Date of Patent: Oct. 23, 2001

(54) METHOD AND APPARATUS FOR PREDICTING THE FLUID CHARACTERISTICS IN A WELL HOLE

(75) Inventor: Brian H. Samaroo, Houston, TX (US)

(73) Assignee: Production Testing Services, Houston, TX (US)

( * ) Notice: Subject to any disclaimer, the term of this patent is extended or adjusted under 35 U.S.C. 154(b) by 0 days.

(21) Appl. No.: 09/469,437

(22) Filed: Dec. 21, 1999

(51) Int. Cl.⁷ .............. G06F 19/00; F16L 9/00; G01N 7/00
(52) U.S. Cl. ............ 73/53.01; 73/53.04; 73/61.44; 73/152.21; 73/152.42; 73/861.04; 73/200; 702/12
(58) Field of Search .................. 73/53.01, 53.04, 73/61.44, 61.47, 61.46, 19.05, 19.1, 30.02, 31.04, 152.18, 152.21, 152.22, 152.52, 152.42, 152.08, 861.04, 196, 200, 866.4, 805, 61.41, 19.11, 152.11; 702/12, 32, 24

(56) References Cited

U.S. PATENT DOCUMENTS

| | | | |
|---|---|---|---|
| 4,657,529 | * | 4/1987 | Prince et al. .............. 604/6 |
| 4,787,421 | * | 11/1988 | Yu .............. 138/178 |
| 5,327,984 | * | 7/1994 | Rasi .............. 175/61 |
| 5,635,631 | * | 6/1997 | Yesudas et al. .............. 73/61.46 |
| 5,924,048 | * | 7/1999 | McCormack et al. .............. 702/13 |
| 5,937,362 | * | 8/1999 | Lindsay .............. 702/9 |
| 5,959,194 | * | 9/1999 | Nenniger .............. 73/53.01 |
| 6,021,664 | * | 2/2000 | Granato et al. .............. 73/53.01 |

* cited by examiner

Primary Examiner—Hezron Williams
Assistant Examiner—David J. Wiggins
(74) Attorney, Agent, or Firm—Wendy K. Buskop; Buskop Law Group, PC

(57) ABSTRACT

An improved apparatus and improved method for determining the characteristics of a multi-phase fluid along a well hole having a predefined geometric profile are presented. Various state properties of the fluid, including the temperature, pressure and specific gravity are taken at the wellhead and used as starting values for calculating estimated state properties at various segments along the well hole. Once the state properties are calculated, an estimated mass flow and velocity rate for the fluid and its constituents can be calculated at specific points along the well hole by implementing computer-based programs and algorithms to extrapolate and/or iterate the known parameters and measurements in a progressively incremented manner from the locations of such given starting points at an initial segment up to other further points corresponding to a set of further sequential segments used in the geometric profile mathematical model.

28 Claims, 4 Drawing Sheets

METHOD AND APPARATUS FOR PREDICTING THE FLUID CHARACTERISTICS IN A WELL HOLE

BACKGROUND OF THE INVENTION

1. Field of the Invention

The present invention relates to oil and gas wells. More particularly, the present invention relates to an improved method and apparatus for predicting the state properties of a multi-phase fluid at any point within the fluid conduit of an oil and gas well.

2. Description of the Related Art

Oil and gas have been extracted from the subsurface of the earth for many decades. Well holes are drilled into the earth until a reservoir of fluid is reached. The underground fluid is then extracted and refined for various purposes. As with most oil and gas wells, the extracted fluid is a multi-phase mixture of oil, water, and gas. The gas itself is in two forms, free gas and gas that is in solution either with the oil or with the water.

The monitoring of the production of fluid from oil and gas wells continues to be an important activity. Not only is monitoring necessary for obvious economic reasons, but also as an indicator of serious problems, such as leaks in the piping making up the well.

Currently, oilfield service companies physically insert a measuring tool into the flow conduit of a well to measure fluid characteristics such as temperature, pressure, and total flow rate. The process of physically measuring and recording the flow in a well hole is called production logging. At best, a production log may provide an accurate snapshot of production information at the particular time that the measurements are made. However, this information can change relatively quickly, especially in a well with multi-zone production where the production from one zone can affect the production in another. There are several other problems involved with prior art production logging methods. First, the measuring device that is used has a finite size, so it disturbs the flow that it is trying to measure and introduces error into the measurement and subsequent calculations. Second, the measuring device must be calibrated in the well. Unfortunately, the well cannot be producing while the measuring device is being calibrated so the calibration period results in a loss of revenue for the oil well owner. Consequently, current production logging methods are not entirely satisfactory.

There has been, therefore, a need, for a variety of methods and/or of devices for production logging that can measure accurately the production capacity of an oil and gas well without disturbing the fluid flow during measurement and more specifically, there exists a need for using two sets of stabilized surface production tests to more accurately predict the results of a well analysis. There is also a need in the art for a method that does not require the well to be shut down during calibration of the measuring instruments for this stabilized data. It is an object of the present invention to solve the problems inherent in the prior art methods and to give an accurate surface production test information. It is a further object of the present invention to utilize existing equipment on the wellhead to enable remote monitoring of well production.

SUMMARY OF THE INVENTION

The present invention solves the problems inherent in the prior art. The evaluation program of the present invention is capable of performing a series of functions necessary to calculate the characteristics of the multi-phase fluid flow along the predefined geometry of the well hole and eliminating or reducing the existence of erroneous surface production test data by providing an accurate data combination by taking data at different points in time in order to determine the existence of accurate stabilized production data for use in well analysis. Using this improvement an evaluation program divides the geometric profile into a series of discrete segments of a predefined thickness, starting at the wellhead and ending at the last reservoir. Starting at the wellhead, the evaluation program trains, segment by segment, wellhead data until the end point is reached. At the starting point, the wellhead temperature and pressure, the wellhead geometric profile, the wellhead gas production rate, and the oil, condensate and water production rates are provided. To determine the conditions at the segment just below the wellhead, the evaluation program extrapolates the temperature profile to estimate the temperature at that particular segment location. Similarly, the geometric profile is extrapolated to determine the geometric configuration of the segment at that particular location in the fluid conduit. Using the total flow rate at the previous step (in this case, at the wellhead), an estimated pressure is calculated for that particular segment. The estimated pressure, estimated temperature, estimated geometry are used to calculate an estimated total flow rate of the fluid in the well hole at that particular location. These estimated values are used to correlate the phase segregation of the fluid at any one segment, and then to act as the initial values for the next segment farther down the well hole. These steps are repeated until the end point of the well hole is reached. The improvement imposes using a pair of stabilized surface production tests to determine if a minimum point exists for the change in pressure with the change in total gas production rate for a given change in total liquid production rate between the two tests. If the minimum point exists then the pair of stabilized surface production test is accurate, if not then the pair of tests is not possible and another pair of tests should be investigated until an accurate pair of tests is found.

This method is also useful for estimating the phase segregation of the fluid in the well. Once the phase segregation can be determined at each step within the well geometry, the constituent flow rates of the gas, water, and oil can also be calculated.

These velocity rates are useful in determining if apparent flow rate losses are due to liquid drop-out (retrograde condensation) of the gas. Furthermore, apparent fluid flow losses or gains at particular steps can be attributed accurately to thief zones or production zones, respectively.

DETAILED DESCRIPTION OF THE PREFERRED EMBODIMENTS

Figure 1:
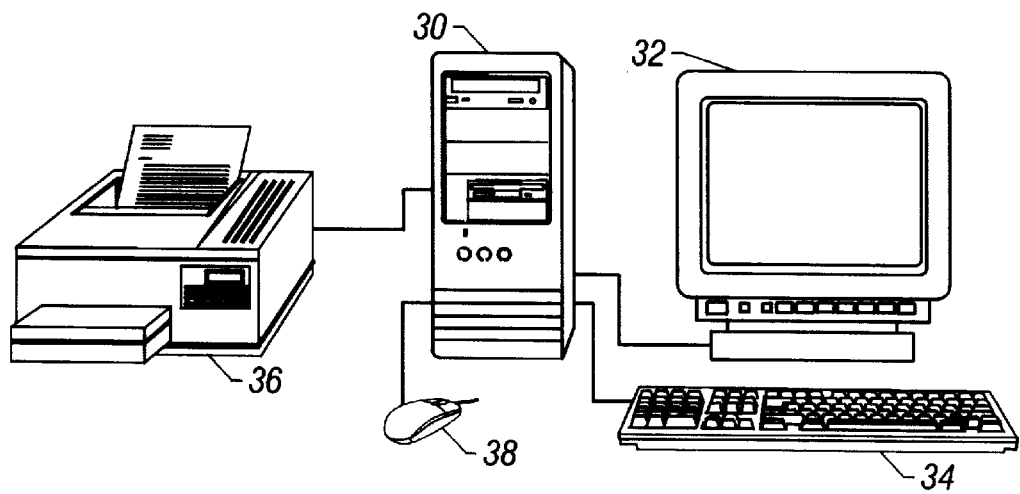
FIG. 1 shows a computer system of the present invention.

The method of the present invention is an improvement over a method using stabilized surface test data to determine fluid properties at the points of influx or efflux in the flow conduit (well hole). The fluid in question can be from any well through which gas and at least one other liquid phase is being commingled and produced. Such a fluid is called a multi-phase fluid. The method of the present invention applies to any well producing either of the following combinations of fluids:

a) gas, oil, and water;

b) gas and oil, c) gas and water, d) gas, condensate, and water, or e) gas and condensate.

This method does not apply to either dry gas well or dead oil wells. In addition, the method of the present invention does not apply to wells on rod pumps where the fluids are separated and the wellhead pressure is near atmospheric pressure.

The method of the present invention determines the flow properties and information such as the depth of production zones (influx) and the depth of thief zones (efflux). The present invention also determines the productivity indexes (PI) or infectivity index (II) of the zones. Points of influx are normally attributed to the following: productive zone, points of liquid channeling into the flow conduit, liquid "drop out" in a gas well, gas injection in a continuous flow gas lifted well, and lift points for a well with an electric submersible pump or hydraulic pump. Points of efflux are normally attributed to the following: thief zones and leaks in the flow conduit.

Another embodiment of the present invention constitutes an improvement which can be applied to an oil or gas well as long as the well produces either of the following fluid types at the wellhead:

a). Gas, oil, and water;

b). Gas and oil; or c). Gas and water.

To perform the method of the original invention, three categories of data were needed:

1) stabilized surface production test data, 2) fluid property data, and 3) the flow conduits geometric profile data.

This improvement requires the following data for each applicable well type:

1). Two stabilized surface production tests. Each test must include the following information:

a). Total gas production rate;

b). Total oil production rate;

c). Total water production rate.

The stabilized surface test data required by the original invention was taken regularly on a producing well, typically at the wellhead. The stabilized surface test data needed was:

a) the wellhead pressure, b) the gas production rate, and c) the oil, condensate, and water production rates.

The use of stabilized surface test data (wellhead data) was preferred because the data was less expensive to obtain than inserting probes into the fluid conduit. Furthermore, unlike the prior art probe insertion method, no well down-time is required for the method of the present invention.

The required fluid property data for the method of the original invention comprised:

a) the API gravity of oil or condensate, b) the specific gravity of water (if any), c) the specific gravity of the gas produced, d) the wellhead temperature, and e) the bottomhole temperature.

The method of the original invention divided the flow conduit into a series of segments. Geometric profile data was needed at each segment. The data needed for each segment included:

a) the true vertical depth, b) the measured depth, and c) the internal diameter (used to calculate the cross-sectional area).

Generally, these data are provided at specific points along the fluid conduit. Data for points in between are interpolated using common algorithms.

The information for the stabilized surface production test needed for this improvement must be different for the two tests except when either the total oil production rate or the total water production is zero for both tests. The improvement requires data known as well fluid PVT data. This data must include the following:

a). API gravity of the oil;

b). Specific gravity of the gas;

c). Specific gravity of the water;

d). Average wellhead temperature; and e). Average bottomhole temperature.

Further for the improvement to work, the measured depth of the wellhead where the wellhead pressure measurements are made must be known. Note that the reference point for this measurement should be the same as for all other measured depth measurements provided in items 4 and 5 to follow;

Also, the measured depth of the end of each segment of tubing of a constant internal diameter and the internal diameter of the segment of tubing must be ascertained. This information should be provided from the wellhead to the bottom of the well; and Additionally, the measured depth and true vertical depth of the end of each segment of tubing of a constant inclination angle (Deviation Survey) is needed to perform the necessary computer calculations. This information should be provided from the wellhead to the bottom of the well.

This well data is what is needed to perform multiphase flow modeling from the wellhead to the bottom of the well of the existing improvement.

The method of the original invention was best accomplished with the use of a digital computer. A software program that embodied the steps proscribed therein was executed on the digital computer to achieve the desired results. As shown in FIG. 1, the improvement uses a computer system comprising a personal computer 30. The average personal computer produced today is sufficient for these purposes. Connected to the computer 30 is a display monitor 32 that is capable of displaying the results from the software program. A keyboard 34 and/or mouse 38 are used to input the data about the well. Optionally, a printer 36 is also connected to the computer 30 so that hard copies of the results from the software program can be produced. In the preferred embodiment of the present invention, a sufficient amount of storage capacity is included with the computer 30 to store all of the fluid information at each segment along the well. The stored information about each segment, along with the input data, can then be presented on display 32 or printed on printer 36.

Figure 2:
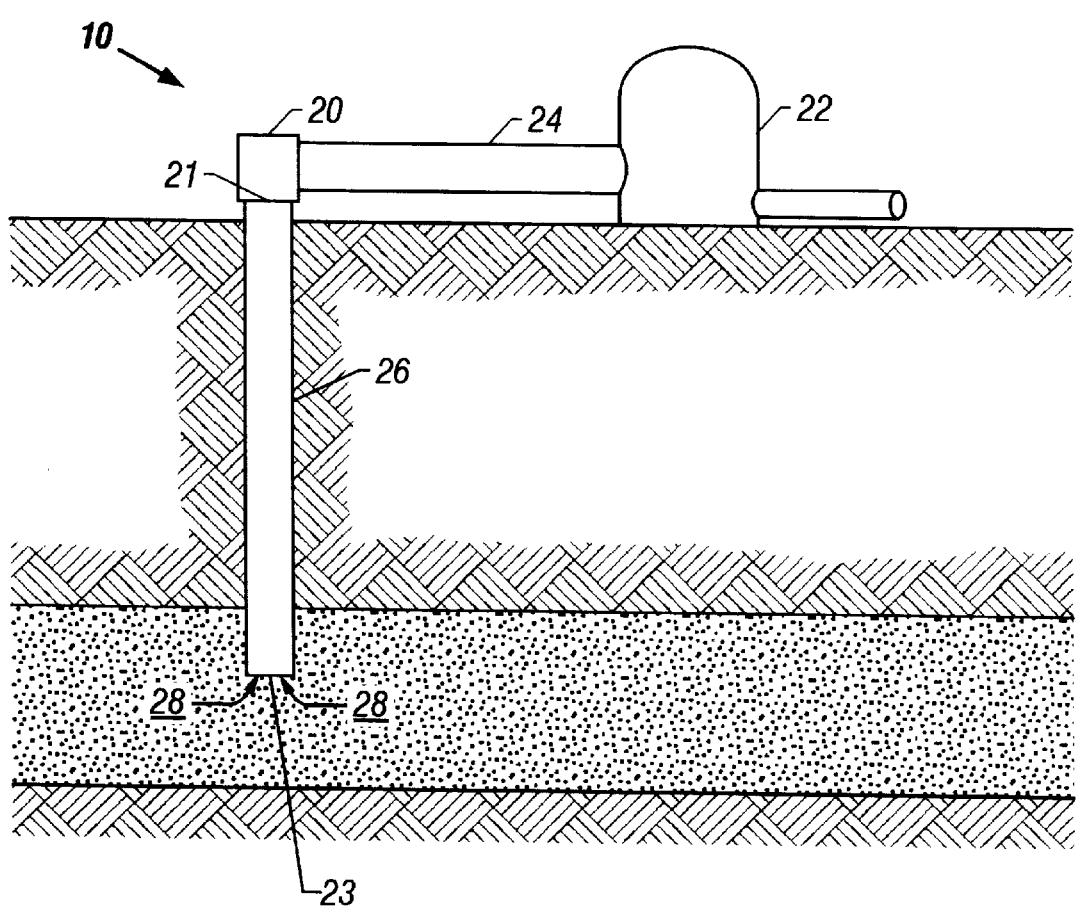
FIG. 2 shows a conventional well hole.

FIG. 2 shows a typical oil and gas well. The well 10 is composed of a reservoir 28 that contains the desired fluid (usually oil and/or natural gas). Pipe 26 is drilled into the ground until it reaches reservoir 28. Once drilled, pipe 26 acts as a conduit to remove the fluid from the reservoir 28. There may be multiple reservoirs along the well 10.

Figure 4:
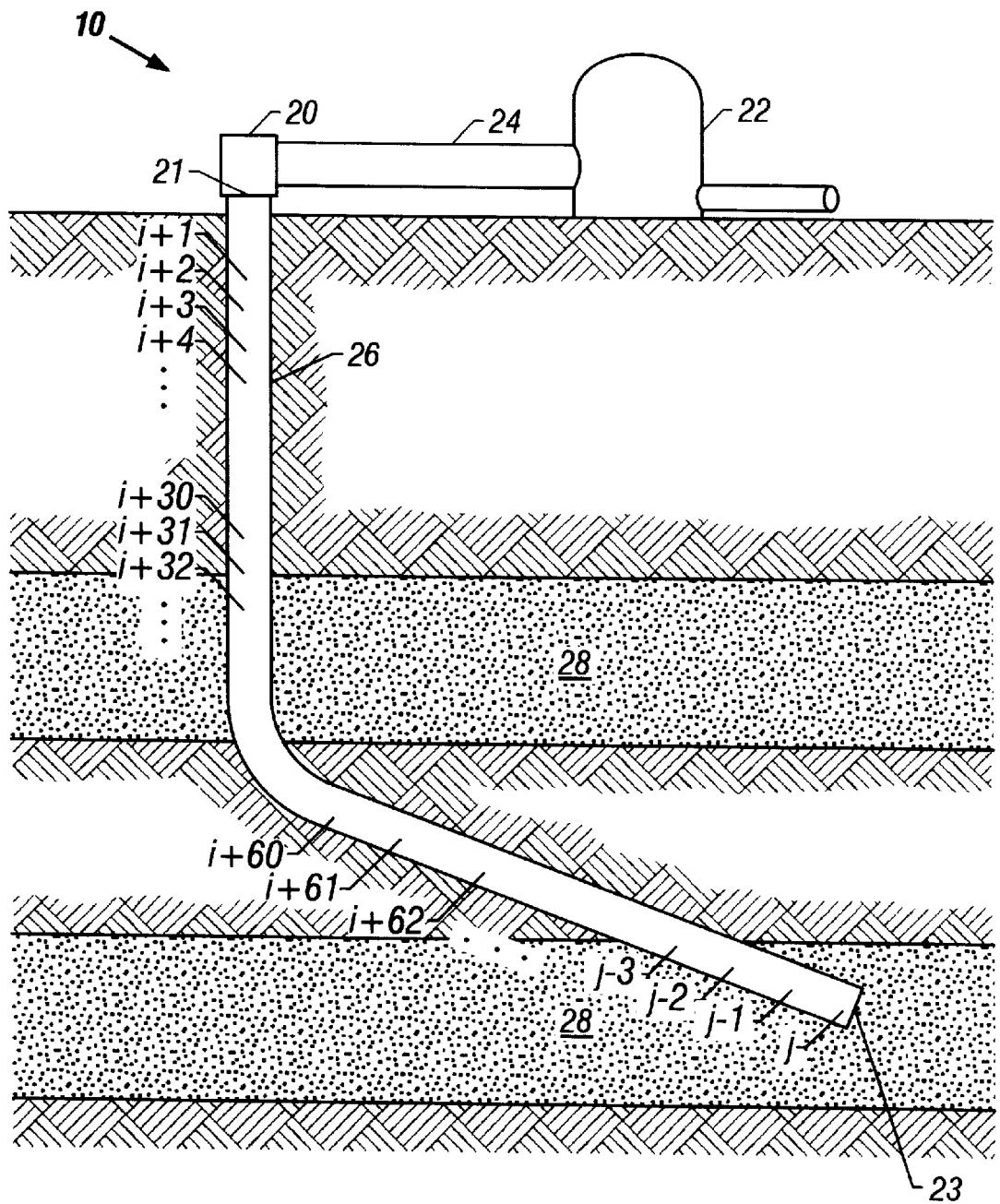
FIG. 4 shows a conventional well hole that is divided into segments.
Figure 5:
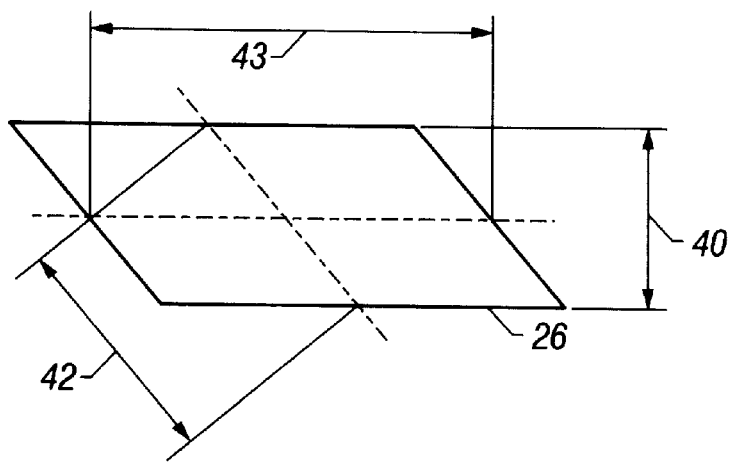
FIG. 5 shows a segment of a fluid conduit.

As shown in FIGS. 2 and 4, the extracted fluid flows from the reservoir 28 to the wellhead 20. An out-take pipe 24 takes the fluid from the wellhead 20 to the separator 22 where the multi-phase fluid is separated into its constituent elements, namely oil, water, and gas. The geometric profile of a typical segment is shown in FIG. 5. Referring to FIG. 5, the geometric profile for each segment comprises the internal diameter 43, the measured depth 42, and the true vertical depth 40. As shown in FIG. 4, the wellhead is defined by the cross sectional area of the well along the hole running from the starting point 21 (typically at the wellhead 20) and the ending point 23 (typically at the last reservoir 28). This cross-sectional area at any given point along the well is designated by the symbol "A." The set of areas along the well hole is designated by the symbol "G." The cross-sectional area usually known at several points along the well. The geometric profile is considered to be predefined for purposes of the present invention and constitutes one set of the input data values. An estimated value of A at any point along the well can be estimated by using standard straight-line or curve interpolation algorithms with G as input to the interpolation algorithm.

As with the geometric profile, the temperature profile of the well from the starting point 21 to the ending point 23 is usually well known. For purposes of this disclosure, the temperature at any given point along the well is designated by the symbol "T." The set of temperature data along the well hole is designated by the symbol "H." The temperature profile H is considered to be predefined for purposes of the present invention and constitutes one set of the input data values. An estimated value of T at any point along the well can be estimated by using standard straight-line or curve interpolation algorithms with H as input to the interpolation algorithm.

Two other parameters, in addition to the temperature T and area A, define the characteristics of the fluid at any given point in the well. Those two parameters are the pressure (designated by the symbol "P") and the total fluid flow rate (designated by the symbol "$W_t$"). The total fluid flow rate $W_t$ is defined by the following formula:

$$W_t = W_o + W_w + W_{gf} + W_{gs}$$

where $W_o$ is the flow rate of oil, $W_w$ is the flow rate of water, $W_{gf}$ is the flow rate of free gas, and $W_{gs}$ is the flow rate of the gas that is in solution. Typically, the pressure and total flow rate are known only at the wellhead. The total flow rate, $W_{ti}$, may itself have been calculated knowing the specific gravity of the fluid at the wellhead. The wellhead pressure and the wellhead total flow rate constitute the final two input data values for the present invention.

Figure 3:
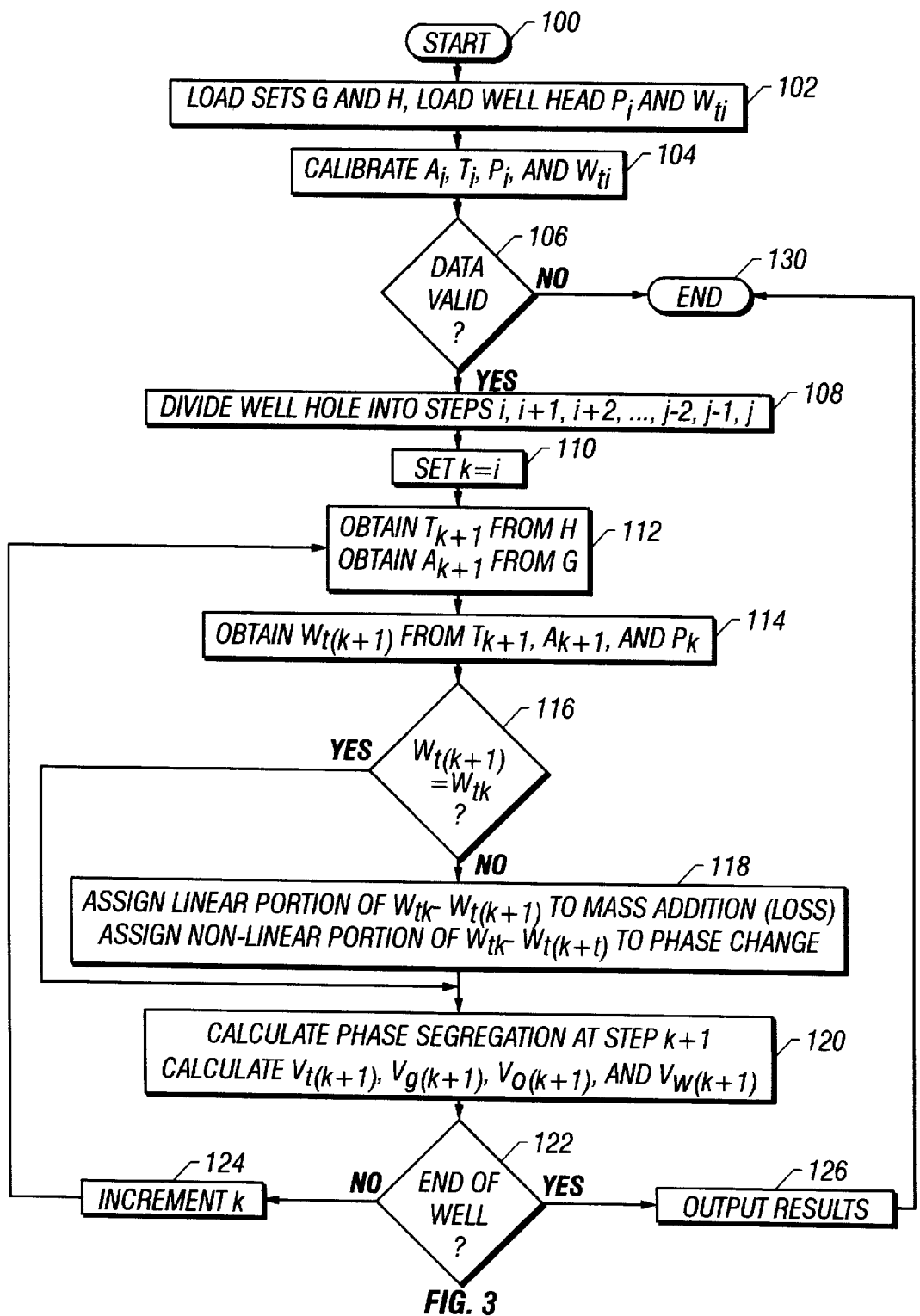
FIG. 3 shows a flowchart of the method of the present invention.

As shown in FIG. 3, the program is started (step 100) and the input data values are read in step 102. The input values consist of the temperature profile H, the geometric profile G, the wellhead pressure $P_i$, and the wellhead total flow rate $W_{ti}$. The input data is calibrated in step 104. In the preferred embodiment of the present invention, a user-friendly software program, called a front-end, performs steps 102 and 104 of FIG. 3 and is used to format the input data for the evaluation program.

The technique for the multi-phase flow correlation is defined by Beggs and Brill. See Beggs, H. D. and Brill, J. P., "A Study of Two-Phase Flow in Inclined Pipes," Journal of Petroleum Technology (Many 1973), pp. 607–619, included herein by reference for all purposes. While there are many multi-phase flow correlations in use today, the Beggs and Brill technique was the simplest to program on a digital computer. It will be understood by those of ordinary skill in the art to use other techniques for multi-phase flow correlation without departing from the scope of this invention.

In order to avoid unnecessary calculation of bad data the calibrated data is checked in step 106. If the input data is bad, the program is terminated immediately in step 130. However, if the data is valid, step 108 is executed.

In step 108, the length of the well hole is divided into equal-length sections. Each section is called a segment and each segment is separated, in the preferred embodiment, by 0.01 feet. Shorter segment lengths increase the accuracy of the results. However, segment lengths less than 0.01 feet do not significantly increase the accuracy. Segment lengths much greater than 0.01 feet generally yield inaccurate results. Longer wells require more segments. Consequently, the computer must have sufficient memory to retain data at each segment if such data are requested by the user. According to step 108 of FIG. 3, each segment is assigned a number. As shown in FIG. 4, the first segment (i) is at the wellhead and the last segment (j) is at the last reservoir. The segments are in sequential order, i.e., i, i+1, i+2, . . . , j–2, j–1, j. Segments at any given point along the well hole are designated by the letter "k," e.g., $T_k$ or $P_k$. Correspondingly, the next segment down-hole after segment k would be segment k+1.

As mentioned previously, the only place where the fluid characteristics are well known is at the wellhead. Thus, $T_i$, $A_i$, $P_i$, and $W_{ti}$ are used as the initial values and are loaded into the k registers of the evaluation program, $T_k$, $A_k$, $P_k$, and $W_{tk}$, respectively (i.e., setting k=i), as shown in step 110 of FIG. 3. The value of k indicates the current segment number.

Given the two surface production tests and other well data PPPM initially calibrates the data to fit the actual well data to the multiphase flow correlation used, which is in the PPPM program the Beggs and Brill correlation, and the various black oil models used. The black oil models used are the more popular ones used and are chosen because of its programming ease. Once calibration is completed the pressure profiles are computed for the surface production tests in the flow conduit. The profiles are computed beginning at the wellhead and moving in an increasing measured depth sequence. This is illustrated in step 112 and 114 in FIG. 3. The changes in the profiles give indications of points of influx or efflux. Once the last section of flow conduit is reached then PPPM calculations are completed.

Once step 118 is complete, or if $W_{t(k+1)}$ and $W_{tk}$ were found to be equivalent in step 116, then step 120 is performed. In step 120, the phase segregation is determined by the multi-phase flow correlation techniques mentioned above. Once the phase segregation is determined, differences between the phases as segment k+1 can be compared to the phase segregation in segment k. These phase segregation differences are used to calculate flow velocities of the various phases, i.e., oil velocity $V_{o(k+1)}$, gas velocity $V_{g(k+1)}$, water velocity $V_{w(k+1)}$ and, finally, the total (average) velocity of the fluid $V_{t(k+1)}$.

In step 122, a check is made to see whether or not all of the segments have been addressed. If so, the results are output in step 126 either to display 32 and or to the printer 36 and the program is terminated. Otherwise, k is incremented in step 124 and the program is continued at step 112. Execution continues until all segments have been addressed (e.g., k=j).

For standard oil and gas wells, the method of the present invention determines the mid-depth of production or injection for each productive or thief zone. This mid-depth of production or injection should correspond to the mid-depth. If it does not, then formation damage and/or plugging of the fluid conduit perforation is indicated. The method of the present invention also determines the depths of liquid "drop-out" of either condensate or water for a gas well producing water and/or condensate. The latter information is necessary for determining the depth at which artificial lift equipment should be set to prevent liquid loading problems in a gas well that is producing water and/or condensate. It should be noted that the method of the present invention can also distinguish between the "drop-out" of condensate or water, and a productive or thief zone. While the absolute value of the PI or II for each zone is itself meaningless, comparison from zone to zone in the same well, or for the same zone in the same well from time to time, can provide accurate results.

For a well on continuous flow gas lift, the method of the present invention determines the gas injection depth. In addition, the as with the well described previously, the method of the present invention can also distinguish between the "drop-out" of condensate or water and productive or thief zone. This index at each depth of gas injection provides a measure of valve performance as the valve sits in the wellbore. For a well using an electric submersible pump (ESP) or hydraulic jet pump or hydraulic piston pump, this index at pump depth provides a measure of pump performance as the pump sits in the wellbore. Finally, this index for the well at each of its productive zones provides a measure of well productivity which, in the prior art, could be obtained only by pulling the pump to test the productive zones.

Figure 6:
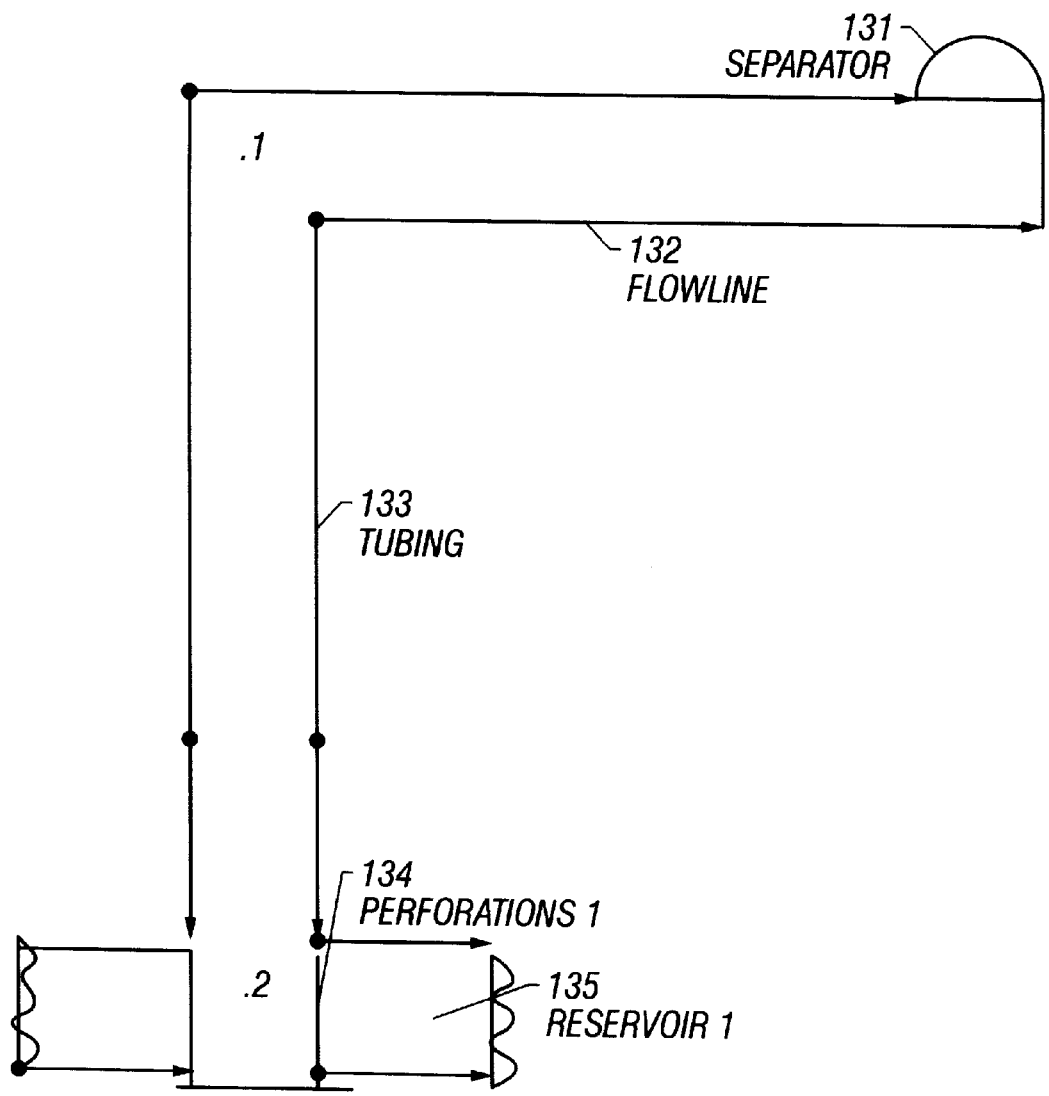
FIG. 6 shows a typical oil or gas well using the present invention.

For the well shown in FIG. 6 in a typical stabilized surface production test the wellhead pressure is measured at Point 1 and the total gas production rate, total oil production rate and total water production rate are all measured at the separator 131 over a test period of approximately 4–24 hours. Excluding the application of the 3PM technology this surface production test data is used to make engineering and economic decisions on the well.

This stabilized surface production test data is normally either totally averaged over the test period or the wellhead pressure portion is taken instantaneously at the end of the test period and the total fluid production rates portion averaged over the test period. Stabilization is assumed to occur over the test period. For either method of taking stabilized surface production test data the following operational problems occur stemming from the fact that although the wellhead pressure is measured instantaneously at the wellhead (Point 1 in FIG. 6) all total fluid production rates are not measured instantaneously but measured over time at the separator some distance from the wellhead (FIG. 6):

1). The total gas production rate at the wellhead is less than the total gas production rate at the separator. The total oil production rate and total water production rate at stock tank conditions are the same as at the wellhead and separator. The reason for the total gas production rate at the separator being larger than the total gas production rate at the wellhead is due to gas increasingly coming out of the solution of the oil as pressure decreases when the oil moves from the higher pressure wellhead to the lower pressure separator; and 2). Fluctuations in flow conditions at the wellhead initiated by the reservoir 135 are felt at the separator after a finite amount of time. The flowline 132 connecting the wellhead to the separator can be quite long increasing this amount of time.

As can be seen these operational problems can cause erroneous stabilized surface production test data regardless of the averaging procedure. This technology utilizes two stabilized surface production tests with each test taken over a different test period. In applying this technology two test periods of tests are needed utilizing data from different parts of each test period to determine the existence of an accurate data combination of two stabilized tests for which to use in the 3PM technology as well as other technologies to for well engineering and well economics purposes.

This technology utilizes The Beggs and Brill $_1$ correlation to perform multiphase flow modeling. In performing multiphase flow modeling Black Oil fluid property correlations are used. Note that the theory behind this technology applies regardless of the type of multiphase flow correlation used as well as the type of Black Oil fluid property correlation used.

In the case of a well having more than one completion this technology can be applied to each completion as long as the above conditions are met.

Also this technology can be applied to a well on artificial lift as long as the above conditions are met.

What is claimed is:

1. An improved method for determining the characteristics of a fluid along a predefined volume having a geometric profile including a starting point and an ending point, a temperature profile, a starting temperature at said starting point, a starting pressure at said starting point, and a starting total flow rate at said starting point, said method comprising the steps of:

(a) dividing said predefined volume into a series of discrete adjacent segments between said starting point and said ending point said series also including a first segment, a next segment, an incrementally progressing segment and a final segment among a multitude of said discrete segments;

(b) interpolating said temperature profile to determine an estimated temperature at the next segment after said starting point;

(c) interpolating said geometric profile to determine an estimated geometry at said next segment;

(d) using said estimated temperature, said estimated geometry, and said starting total flow rate to calculate an estimated pressure at said next segment;

(e) using said estimated pressure, said estimated temperature, and said estimated geometry to calculate an estimated total flow rate at said next segment;

(f) using said estimated pressure, said estimated temperature, said estimated geometry, and said estimated total flow rate as a starting pressure, a starting temperature, a starting geometry, and a starting total flow rate, respectively, for the incrementally progressing segment subsequent to said next segment;

(g) performing steps (b)–(f) until a next segment that corresponds to the final segment with said ending point is reached;

(h) repeating steps (a) to (g) above to acquire a plurality of sets of characteristics of a fluid along a predetermined volume during, different test periods; and (i) performing multiphase flow modeling using said characteristics of a fluid undergoing a flow behavior to determine if a minimum point exists for each set of characteristics of said fluid, thereby determining whether a change in the fluid moving along the predetermined volume occurred.

2. A method as in claim 1 wherein said fluid has an oil phase, a water phase, a free gas phase and an in-solution gas phase.

3. A method as in claim 2 wherein after performing step (e), but before performing step (f), said estimated total flow rate is compared to said starting total flow rate.

4. A method as in claim 3 wherein, if said estimated total flow rate is not equivalent to said starting total flow rate then calculating a total flow rate differential.

5. A method as in claim 4 wherein said total flow rate differential has a linear component and a non-linear component.

6. A method as in claim 5 wherein said linear component of said differential is attributed to a phase change of said fluid between said starting segment and said next segment.

7. A method as in claim 5 wherein said non-linear component of said differential is attributed to a change in the mass of said fluid at said next segment.

8. A method as in claim 7 wherein a positive non-linear component indicates a loss of fluid at said next segment.

9. A method as in claim 7 wherein a negative non-linear component indicates an addition of fluid at said next segment.

10. A method as in claim 6 wherein said phase change can be attributed to retrograde condensation.

11. A method as in claim 1 wherein after step (e), but before step (f), using said estimated pressure, said estimated temperature, said estimated geometry, and said estimated total flow rate to calculate an estimated total flow velocity at said next segment.

12. A method as in claim 11 wherein said estimated pressure, said estimated temperature, said estimated geometry, and said estimated total flow rate are used to calculate an estimated phase distribution of said fluid at said next segment.

13. A method as in claim 12 wherein said estimated phase distribution and said estimated total flow velocity is used to calculate a gas velocity, a water velocity, and an oil velocity.

14. A method as in claim 1 wherein said starting total flow rate is determined from the specific gravity of said fluid at said starting point.

15. A method as in claim 1 wherein the distance between said segments is 0.01 feet.

16. A method as in claim 1 wherein, before step (a), said starting temperature, said starting pressure, said starting geometry, and said starting total fluid flow rate are calibrated.

17. In a computer device having a display device, an entry device, a storage device, and a processor for executing an evaluation program, said evaluation program capable of reading a geometric profile including a starting point and an ending point of a predefined geometric of a fluid flow volume, a temperature profile, a starting temperature at said starting point, a starting pressure at said starting point, and a starting total flow rate at said starting point, said device further capable of performing the following functions:

(a) dividing said predefined volume into a series of discrete adjacent segments between said starting point and said ending point said series also including a first segment, a next segment, an incrementally progressing segment and a final segment among a multitude of said discrete segments;

(b) interpolating said temperature profile to determine an estimated temperature at the next segment after said starting point;

(c) interpolating said geometric profile to determine an estimated geometry at said next segment;

(d) using said estimated temperature, said estimated geometry, and said starting total flow rate to calculate an estimated pressure at said next segment;

(e) using said estimated pressure, said estimated temperature, and said estimated geometry to calculate an estimated total flow rate at said next segment;

(f) using said estimated pressure, said estimated temperature, said estimated geometry, and said estimated total flow rate as a starting pressure, a starting temperature, a starting geometry, and a starting total flow rate, respectively, for the incrementally progressing segment subsequent to said next segment;

(g) performing steps (b)–(f) a next segment that corresponds to the final segment with until said ending point is reached;

(h) repeating steps (a) to (g) above to acquire a plurality of sets of characteristics of a fluid along a predetermined volume during, different test periods; and (i) performing multiphase flow modeling using said characteristics of a fluid undergoing a flow behavior to determine if a minimum point exists for each set of characteristics of said fluid, thereby determining whether a change in the fluid moving along the predetermined volume occurred.

18. A device as in claim 17, said device further capable of displaying said estimated temperature at each of said segments.

19. A device as in claim 18, said device further capable of displaying said estimated pressure at each of said segments.

20. A device as in claim 18, said device further capable of displaying said estimated total flow rate at each of said segments.

21. A device as in claim 18, said device further capable of displaying said estimated geometry at each of said segments.

22. A device as in claim 18, said device further capable of displaying geologic loss and addition to said estimated total fluid flow rate at each of said segments.

23. A device as in claim 18, said device further capable of displaying the amount of retrograde condensation at each of said segments.

24. A device as in claim 18, said device further capable of displaying the phase segregation of a multi-phase fluid at each of said segments.

25. A device as in claim 18, said device further capable of displaying the velocity of said fluid at each of said segments.

26. A device as in claim 18, said device further capable of displaying the velocity of the gas that makes up a part of said fluid at each of said segments.

27. A device as in claim 18, said device further capable of displaying the velocity of the oil that makes up part of said fluid at each of said segments.

28. A device as in claim 18, said device further capable of displaying the velocity of the water that makes up a part of said fluid at each of said segments.

* * * * *